US011026698B2

(12) United States Patent
Orbay et al.

(10) Patent No.: US 11,026,698 B2
(45) Date of Patent: Jun. 8, 2021

(54) OSTEOTOMY SYSTEM AND METHOD OF USE

(71) Applicant: Skeletal Dynamics, Inc, Miami, FL (US)

(72) Inventors: Jorge L. Orbay, Miami, FL (US); Brian A. Cooke, Miami, FL (US); Edward J. Tremols, Miami, FL (US)

(73) Assignee: Skeletal Dynamics, Inc., Miami, FL (US)

( * ) Notice: Subject to any disclaimer, the term of this patent is extended or adjusted under 35 U.S.C. 154(b) by 0 days.

(21) Appl. No.: 17/082,862

(22) Filed: Oct. 28, 2020

(65) Prior Publication Data

US 2021/0137534 A1 May 13, 2021

Related U.S. Application Data

(60) Provisional application No. 62/927,325, filed on Oct. 29, 2019.

(51) Int. Cl.
| | |
|---|---|
| *A61B 17/15* | (2006.01) |
| *A61B 17/17* | (2006.01) |
| *A61B 17/80* | (2006.01) |
| *A61B 90/00* | (2016.01) |

(52) U.S. Cl.
CPC ........ *A61B 17/151* (2013.01); *A61B 17/1728* (2013.01); *A61B 17/1796* (2013.01); *A61B 17/80* (2013.01); *A61B 90/39* (2016.02)

(58) Field of Classification Search
CPC .... A61B 17/151; A61B 17/1728; A61B 17/80
See application file for complete search history.

(56) References Cited

U.S. PATENT DOCUMENTS

| | | | | |
|---|---|---|---|---|
| 3,400,711 | A * | 9/1968 | Frick | A61B 17/8019 606/105 |
| 3,866,607 | A * | 2/1975 | Forsythe | A61B 17/8019 606/105 |
| 4,811,877 | A * | 3/1989 | Heideman | B60R 9/045 224/321 |
| 4,929,247 | A | 5/1990 | Rayhack | |
| 5,042,983 | A * | 8/1991 | Rayhack | A61B 17/15 606/87 |
| 7,540,874 | B2 | 6/2009 | Trumble et al. | |
| 8,652,142 | B2 | 2/2014 | Geissler | |
| 9,023,052 | B2 | 5/2015 | Lietz et al. | |
| 9,902,498 | B2 * | 2/2018 | Gensch | B60N 2/01575 |

(Continued)

OTHER PUBLICATIONS

International Application No. PCT/US20/57845—Patent Cooperation Treaty PCT International Search Report—Completed Dec. 28, 2020 (dated Jan. 27, 2021).

(Continued)

*Primary Examiner* — Christian A Sevilla
(74) *Attorney, Agent, or Firm* — Lott & Fischer, PL

(57) ABSTRACT

Disclosed is a bone cutting and shortening system and the method of using the same, the system comprising a bone plate and a cutting guide adapted to slidingly engage by inserting the cutting guide into the bone plate from the overhead direction, the cutting guide adapted to facilitate parallel cutting planes on a bone at precisely ascertainable offset distances, and the bone plate adapted to stabilize the shortened bone after cutting.

12 Claims, 11 Drawing Sheets

(56) References Cited

U.S. PATENT DOCUMENTS

| | | |
|---|---|---|
| 2007/0276383 A1 | 11/2007 | Rayhack |
| 2010/0168799 A1* | 7/2010 | Schumer ............ A61B 17/8014 606/286 |
| 2011/0238068 A1* | 9/2011 | Bernsteiner ............ A61B 17/15 606/70 |
| 2013/0253592 A1* | 9/2013 | Larche ............... A61B 17/8019 606/282 |
| 2016/0235454 A1 | 8/2016 | Treace et al. |
| 2018/0049785 A1* | 2/2018 | Langdale ........... A61B 17/8605 |

OTHER PUBLICATIONS

International Application No. PCT/US20/57845—Patent Cooperation Treaty PCT Written Opinion of the International Searching Authority—Completed Dec. 28, 2020 (dated Jan. 27, 2021).

* cited by examiner

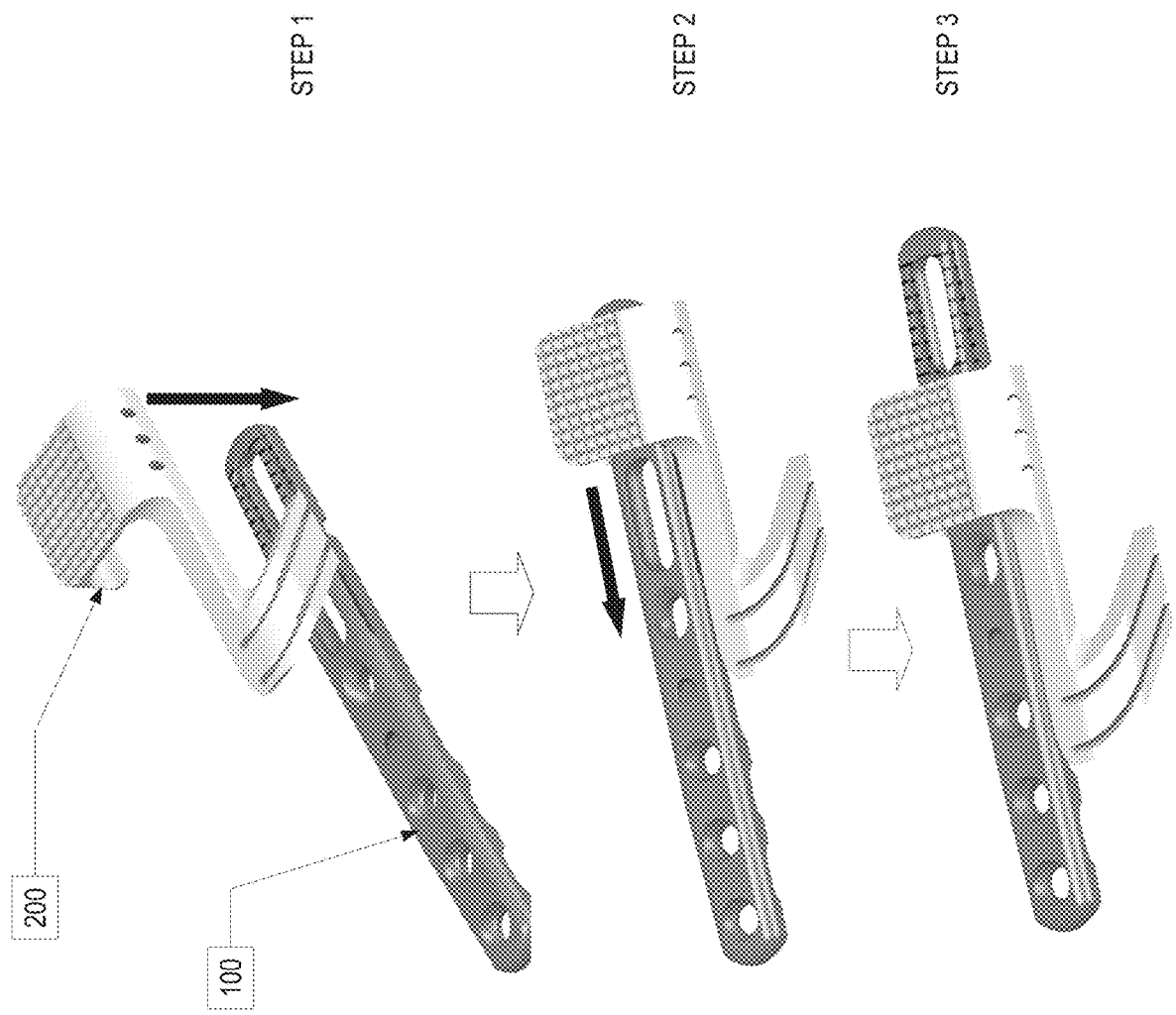

US 11,026,698 B2

OSTEOTOMY SYSTEM AND METHOD OF USE

CLAIM OF PRIORITY

This application is being filed as a non-provisional patent application under 35 U.S.C. § 111(a) and 37 CFR § 1.53(b). This application claims priority under 35 U.S.C. § 119(e) to U.S. provisional patent application Ser. No. 62/927,325 filed on Oct. 29, 2019, the contents of which are incorporated herein by reference

FIELD OF INVENTION

The invention relates generally to orthopedic implants and surgical devices and systems, and, in particular, to a plate and cutting guide system for use in bone osteotomy surgery and to stabilize a shortened bone, including but not limited to, the ulnar bone.

BACKGROUND OF THE INVENTION

To treat certain orthopedic conditions and injuries, it is sometimes necessary to shorten a bone. Most commonly this is accomplished by performing an osteotomy, in which a portion of the bone is cut and removed, the ends of the bone are joined and stabilized, and the bone is held in compression to promote fusion of the ends, resulting in an overall reduction of the bone's length. Described herein is a system comprising a bone plate and a cutting guide which facilitate performance of an osteotomy and stabilization of the shortened bone.

SUMMARY OF THE INVENTION

It is an object of the instant invention to provide a bone cutting system comprising a bone plate and a cutting guide adapted to slidingly engage by inserting the cutting guide into the bone plate from the overhead direction, the cutting guide adapted to facilitate parallel cutting planes on a bone at readily ascertainable offset distances.

The bone plate comprises a substantially rigid plate including an elongated body having a proximal end and a distal end and defining a longitudinal body axis; the plate comprising a bone contacting side, and opposing side, a left sidewall and a right sidewall, all of which extend between the proximal end of the plate and the distal end of the plate and all of which are substantially aligned with the longitudinal body axis; a proximal elongated slot extending through the plate between the opposing side and the bone contacting side located adjacent to the proximal end of the plate, the proximal elongated slot adapted to receive a bone screw; a distal elongated slot extending through the plate between the opposing side and the bone contacting side and adjacent to the proximal elongated slot but located distally on the plate relative to the proximal elongated slot, the distal elongated slot adapted to receive a bone screw; one or more bone screw holes extending through the plate between the opposing side and the bone contacting side and located distally on the plate relative to the distal elongated slot, the one or more screw holes adapted to receive a bone screw; a recess on the opposing side of the plate; a left track recessed into the left sidewall, the left track extending longitudinally between a track limit point and the proximal end of the plate, the left track being bound by an upper bounding wall, and a lower bounding wall, the lower bounding wall extending for the entire length of the left track while the upper bounding wall extends partially from the distal end of the left track to a location distal to the proximal end of the left track; and a right track recessed into the right sidewall, the right track extending longitudinally between a track limit point and the proximal end of the plate, the right track being bound buy an upper bounding wall, and a lower bounding wall, the lower bounding wall extending for the entire length of the right track while the upper bounding wall extends partially from the distal end of the right track to a location distal to the proximal end of the right track; wherein the portions of the left track and the right track that are bound only by a lower bounding wall provide an overhead entry to the left track and right track accessible from the opposing side of the plate.

The cutting guide comprises a handling feature; left and right guide walls extending downwardly from the handling feature and terminating respectively in left and right horizontal guide blades, the left and right horizontal blades adapted to mate with the left and right tracks of the bone plate respectively; an arm extending downward from one of the handling feature, the right guide wall and the left guide wall, and comprising a flange; a cutting slot disposed on the flange; wherein when the left and right horizontal blades are engaged with the left and right tracks of the bone plate respectively; the cutting guide slides in a proximal-distal direction relative to the bone plate.

BRIEF DESCRIPTION OF THE DRAWINGS

FIG. 3 illustrates the sequence for assembly of the bone plate and bone cutting guide shown in FIGS. 1A-E and 2A-C.

DETAILED DESCRIPTION OF THE INVENTION

Figure 1A:
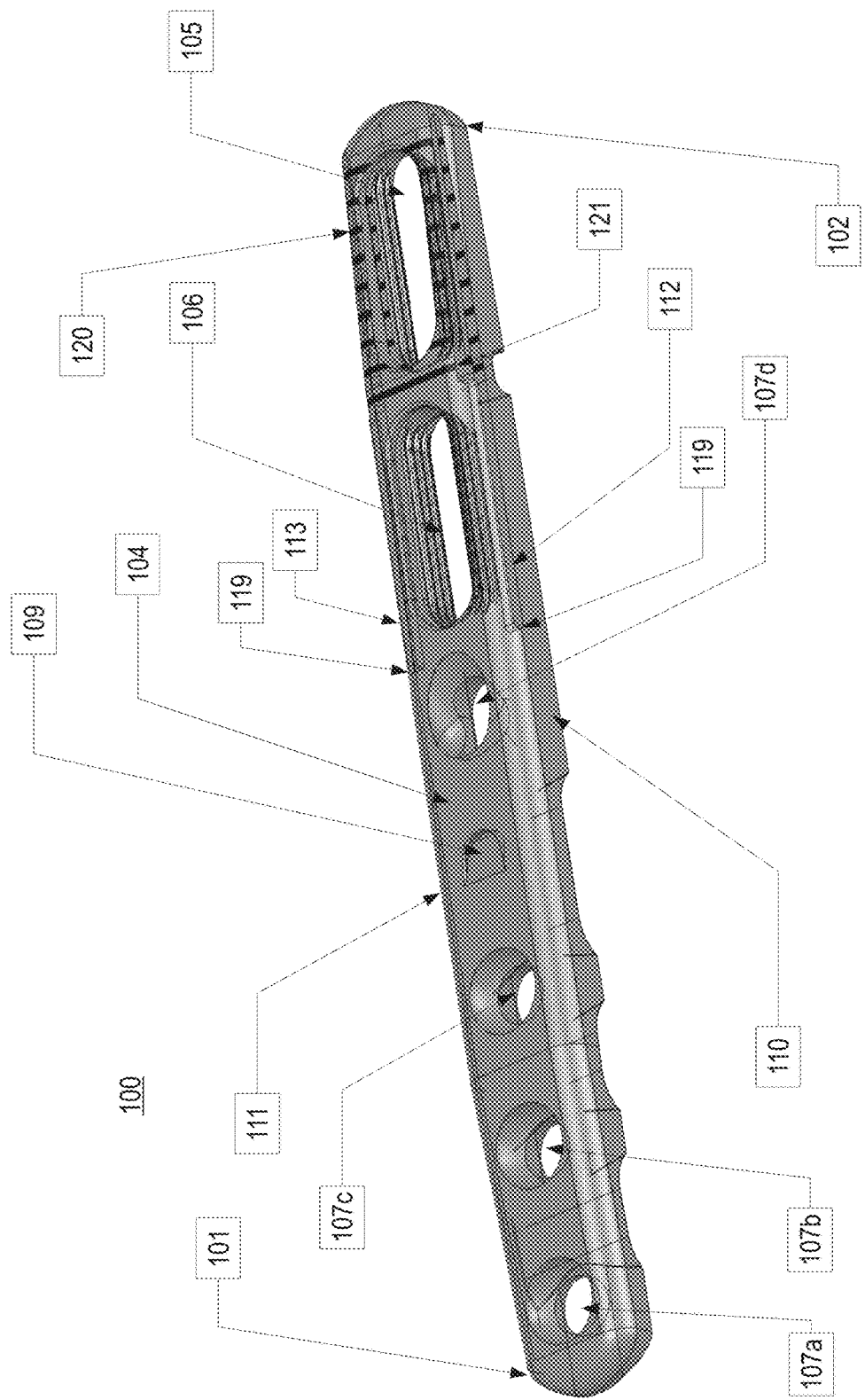
FIG. 1A illustrates a top isometric view of a bone plate according to one embodiment of the present invention adapted for use in an ulnar shortening osteotomy.
Figure 1B:
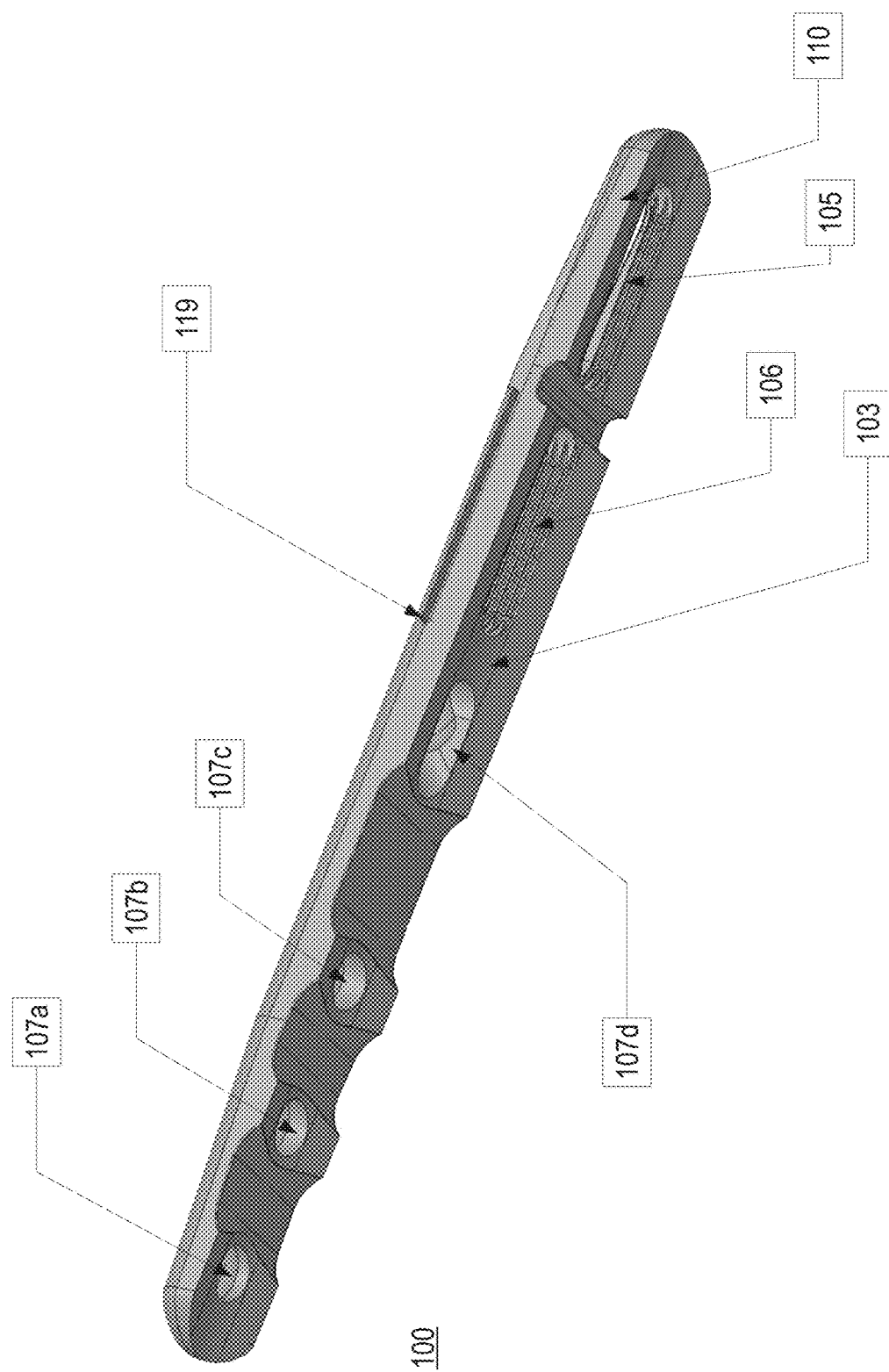
FIG. 1B illustrates a bottom isometric view of a bone plate according to the embodiment shown in FIG. 1A.
Figure 1C:
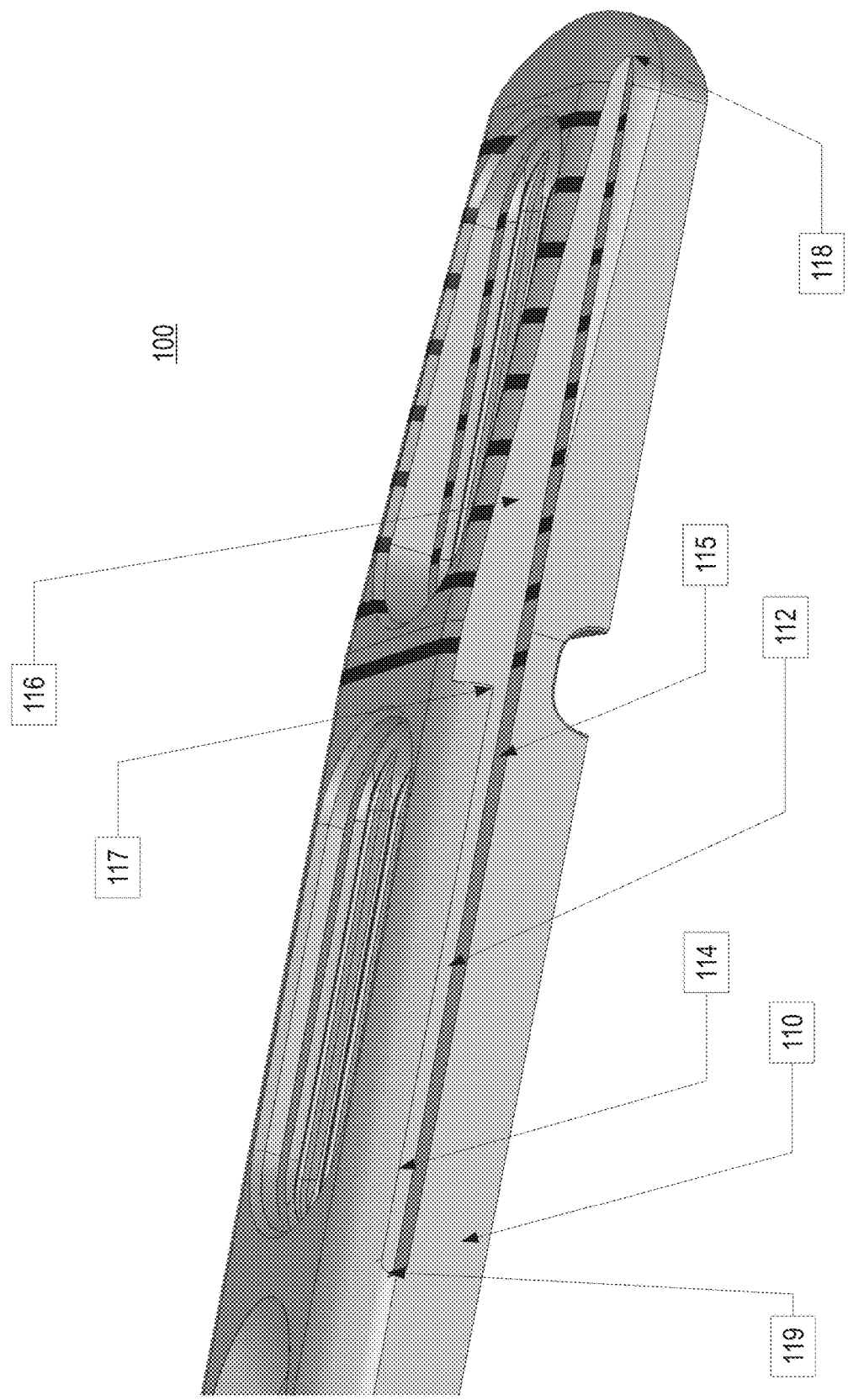
FIG. 1C illustrates a detailed view of the guiding track of the bone plate shown in FIGS. 1A and 1B.

Referring to FIGS. 1A-E, shown are various views of a bone plate (100) according to one embodiment of the present invention adapted to perform an ulnar shortening osteotomy. The bone plate shown is used to guide the surgeon, together with the cutting guide shown in FIG. 2, to precisely cut the desired length from the ulnar bone, to rejoin the two ends of the bone, and to stabilize the rejoined bone ends in compression to promote their subsequent fusion.

The bone plate (100) comprises a substantially elongated metal plate having tapered distal (101) and proximal (102) ends. The bone plate (100) further comprises a bone contacting side (103) and an opposite side (104) a left sidewall (110) and a right sidewall (111). The bone contacting side has a generally cylindrical concave shape which generally conforms, or can be bent to conform, the contour of the bone to be treated. The bone plate also includes a proximal elongated slot (105) and a distal elongated slot (106) which can be threaded or unthreaded. The bone plate (100) further comprises one or more threaded or unthreaded bone screw holes (107a-d,) suitable for cortical bone screws or pegs. Some of the bone screw holes (107a,107b, 107c) may be adapted for installation of bone screws substantially normal to the bone contacting surface, while others (107d) may be adapted for installation of oblique screws. Oblique screws are particularly useful to apply additional compression to rejoined bone ends that have been cut at an oblique angle where the screw can be inserted substantially normal to the angle of the cut. Disposed on the opposing side (104) of bone plate (100) is a recess (109) adapted to receive the tip of a reduction forceps.

Located respectively in the left and right sidewalls (110, 111) of bone plate (100) are a left track (112) and a right track (113) extending longitudinally along the length of bone plate (100). Tracks (112,113) extend proximally from a track limit point (119). In the shown embodiment, the left and right tracks (112,113) are mirror images and substantially identical with symmetrical placement along the left and right walls (110,111) respectively. However, this is not necessary as long as the tracks are adapted to engage corresponding features (shown in figures described below) in cutting guide (200). As shown in detail in FIG. 1C which applies to either left track (112) or right track (113) of the illustrated embodiment (left track (112) is shown for illustration purposes only), the track comprises an upper bounding wall (114) and a lower bounding wall (115). Lower bounding wall (115) extends for the entire length of the track while the upper bounding wall (114) only extends partially from the distal end of the track (119) to a location (117) before the proximal end of the track (118) creating an overhead entry (116) to the track.

Figure 1D:
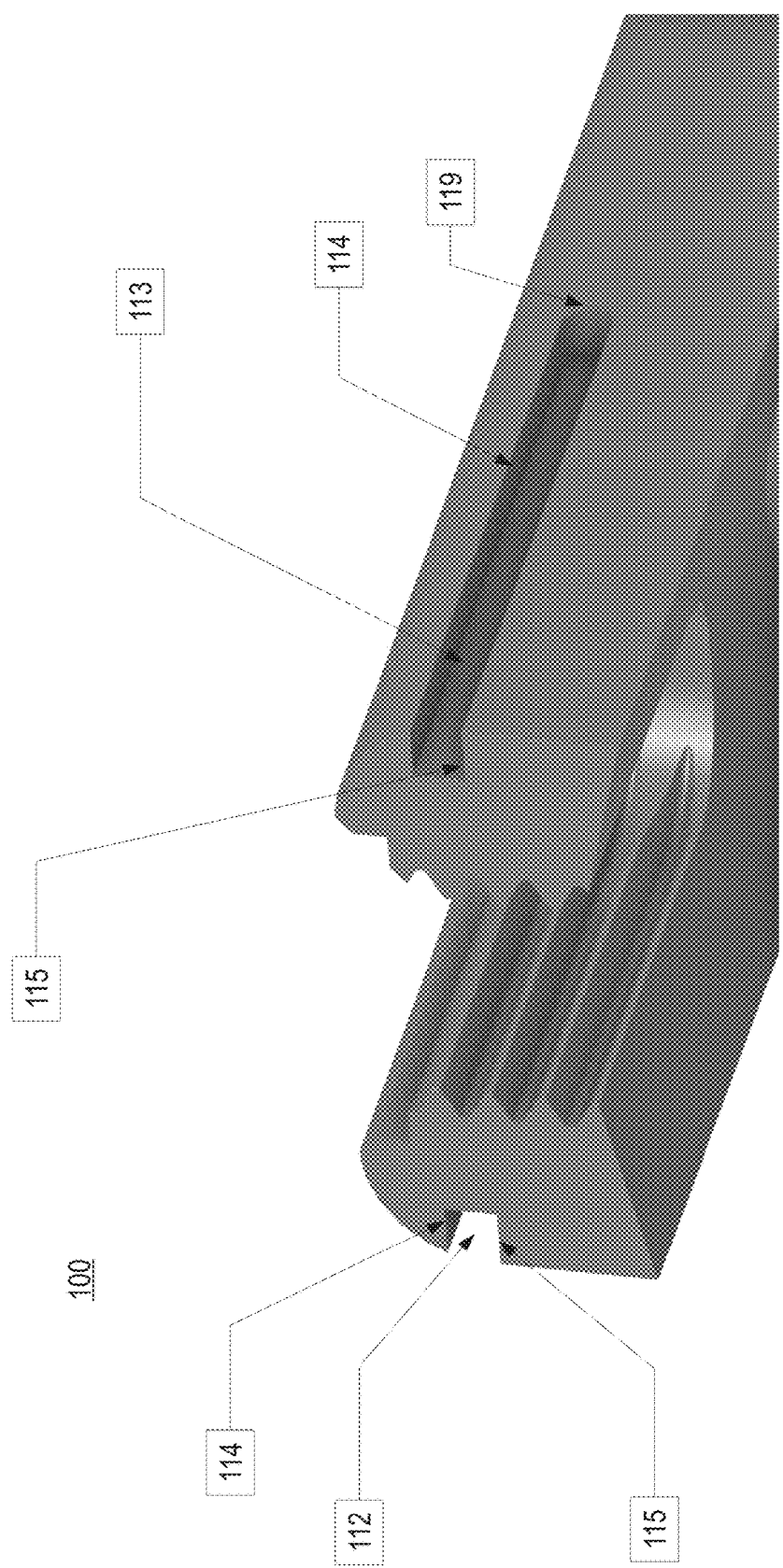
FIG. 1D illustrates a cross-sectional view of the bone plate shown in FIGS. 1A and 1B taken from a location having upward and downward bound track.
Figure 1E:
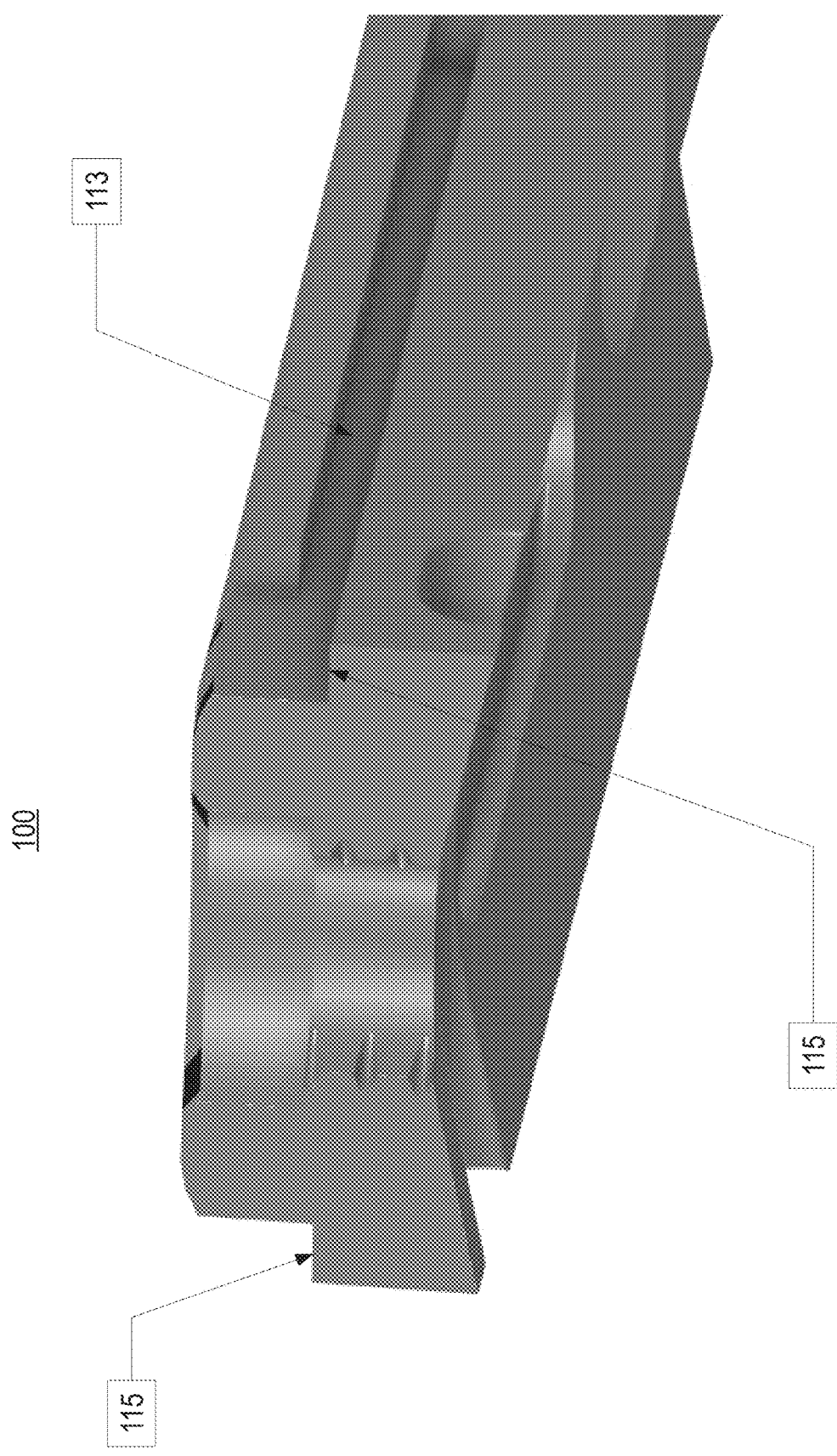
FIG. 1E illustrates a cross-sectional view of the bone plate shown in FIGS. 1A and 1B taken from a location showing having only downward bound track.

The relationship between the left (112) and right (113) can be more clearly seen in FIGS. 1D and 1E. FIG. 1D shows a cross-section of bone plate (100) at a location where the tracks are bound by the upper and lower bounding walls (114, 115). FIG. 1E shows a cross-section of bone plate (100) at a location where the tracks are bound only by the lower bounding wall (115).

Laser etched, or otherwise affixed to the opposing side (104) of the bone plate (100) is a series of indicia (120), including a zero-mark line (121) used to measure the proximal-distal movement of the cutting guide (200) relative to the bone plate (100)

Figure 2A:
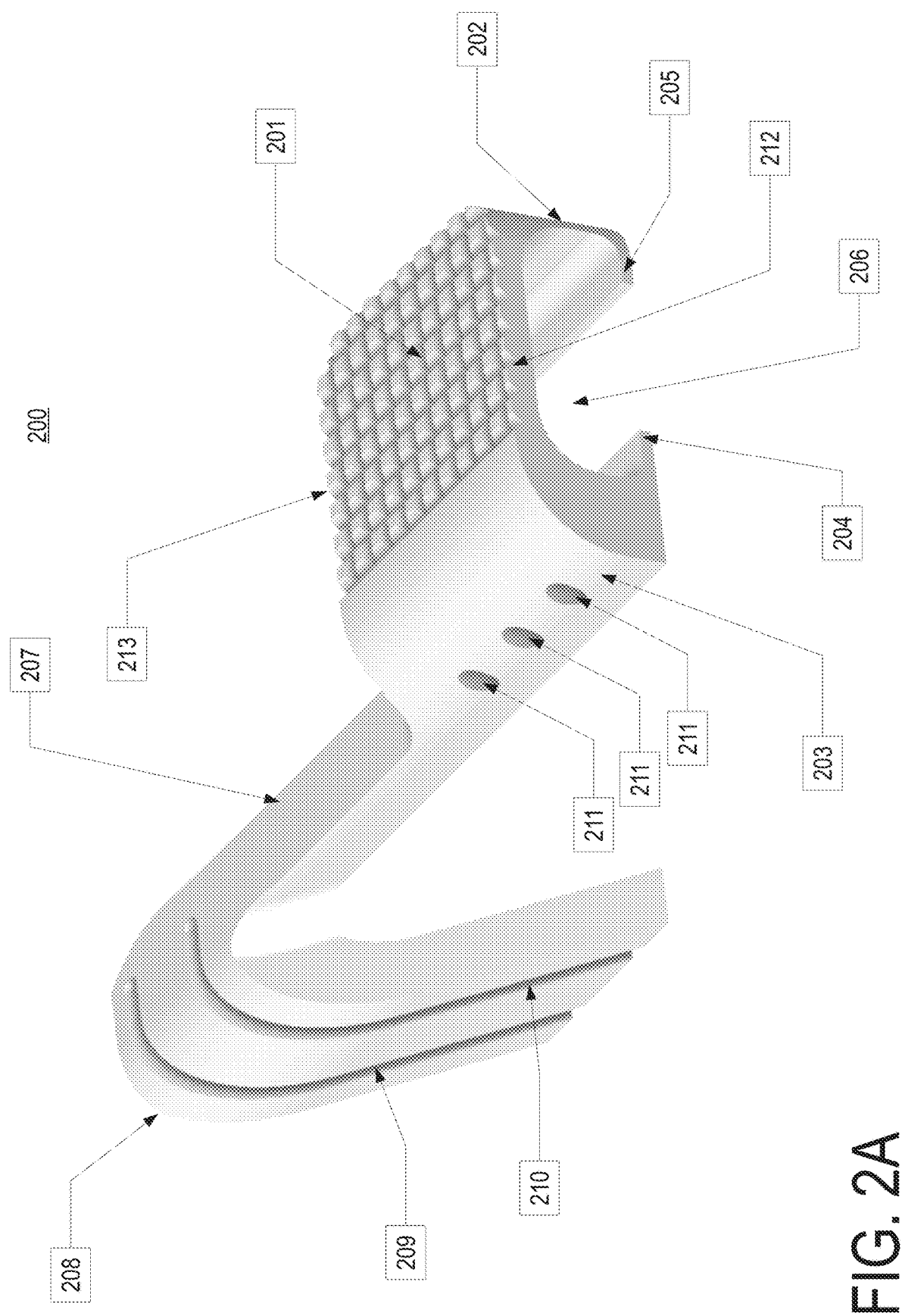
FIG. 2A illustrates a top isometric view of a bone cutting guide according to one embodiment of the present invention adapted for use in an ulnar shortening osteotomy.
Figure 2B:
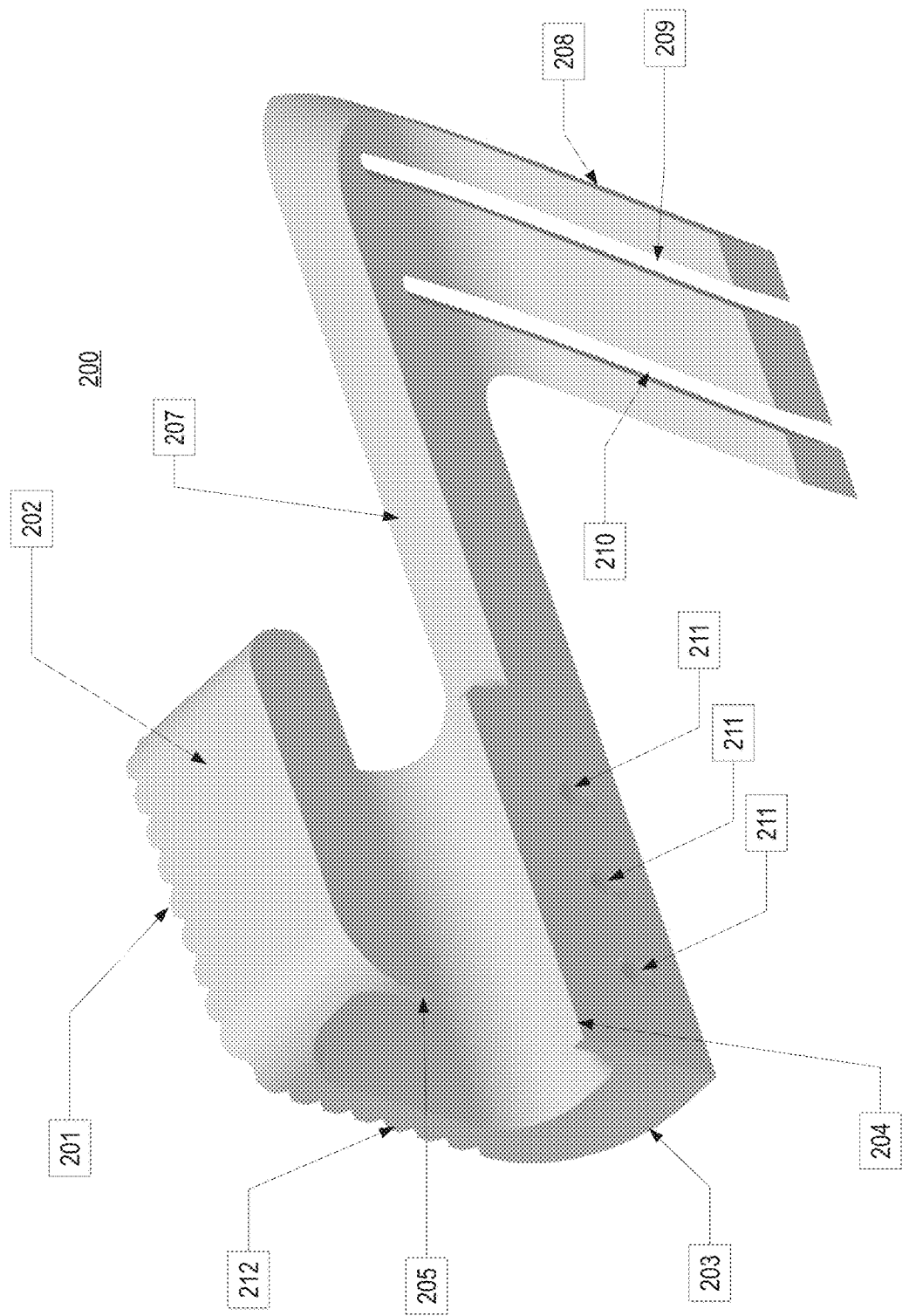
FIG. 2B illustrates a bottom isometric view of a bone cutting guide according to the embodiment shown in FIG. 2A.
Figure 2C:
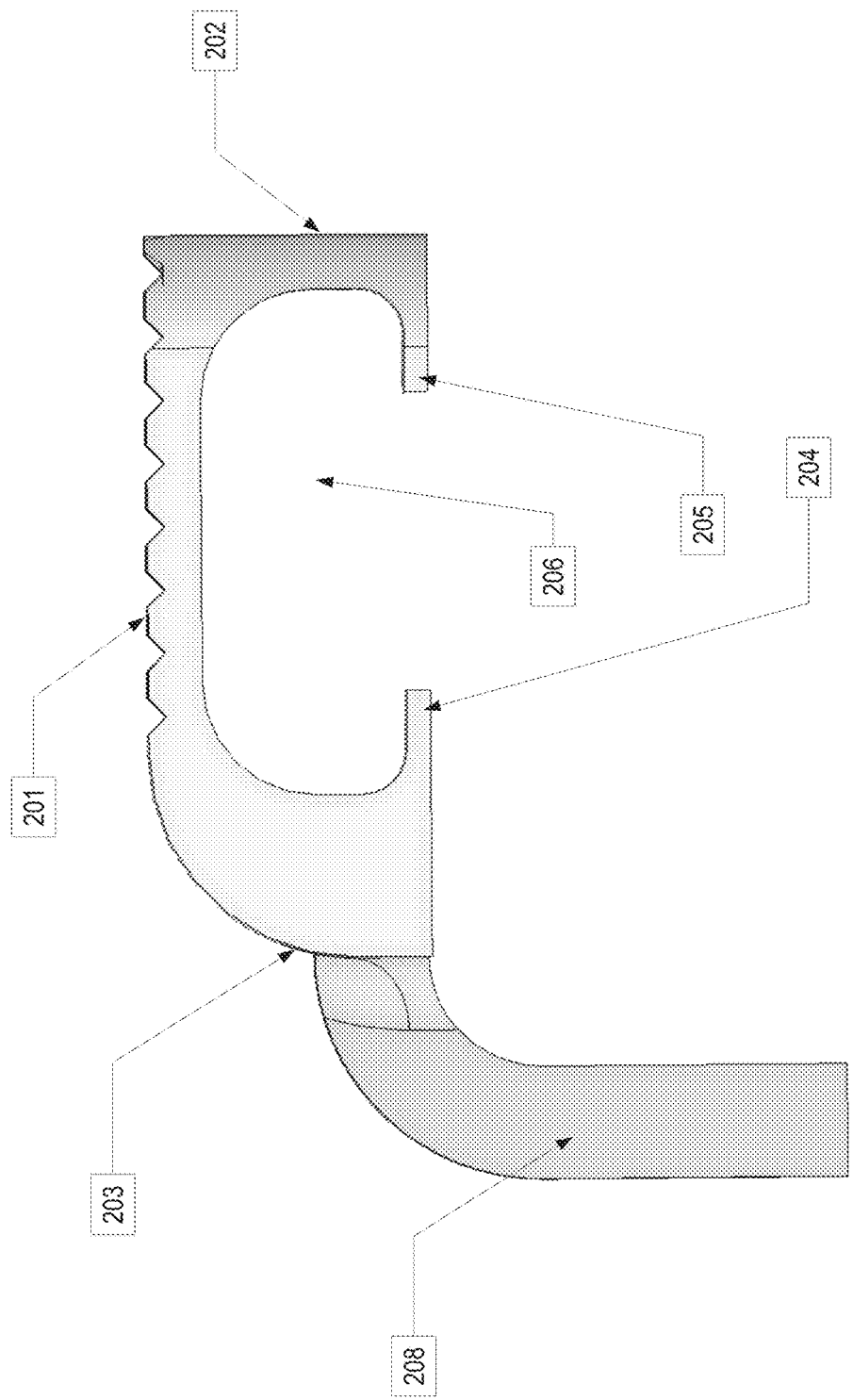
FIG. 2C illustrates a rear elevational view of the bone cutting guide shown in FIGS. 2A and 2B.
Figure 4:
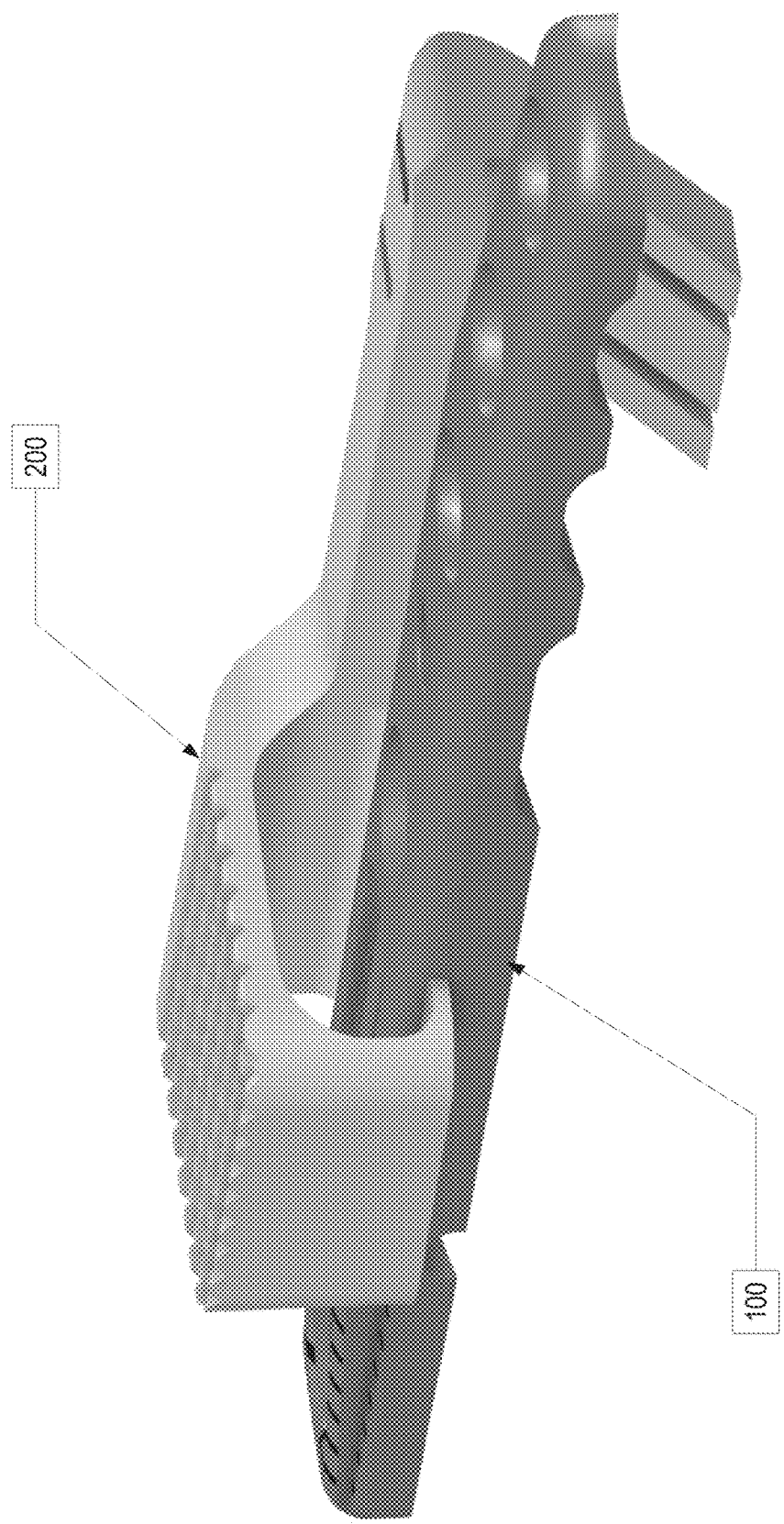
FIG. 4 illustrates the bone plate and bone cutting guide of FIGS. 1A-E and 2A-C after assembly.

Referring next to FIGS. 2A-C shown are various views of a bone cutting guide (200) according to one embodiment of the present invention adapted to perform an ulnar shortening osteotomy. The shown embodiment of bone cutting guide (200) is adapted to cooperate with the bone plate (100) shown in FIGS. 1A-E. The bone cutting guide (200) comprises a handling feature (201) which can optionally be textured and oriented in a generally horizontal plane having proximal and distal edges (212,213). Extending downwardly from the left and right side of the handling feature (201) respectively are guide walls (202,203) which terminate in left (204) and right (205) horizontal guide blades. The left and right guide blades (204,205) are situated on the bone cutting guide (200) so as to precisely mate with the left and right tracks (112,113) of the bone plate (100). The interior space (206) bounded by the handling feature (201), guide walls (202,203) and the left and right guide blades (204,205) is sufficiently large to permit the bone plate (100), once the guide blades (204,205) are mated to the tracks (112,113), to glide in the proximal-distal direction without interference from the bone cutting guide (200). Of course, the distal movement of the cutting guide (200) will be constrained by the track limit point (119).

The cutting guide further comprises an arm (207) which extends distally from one side (left or right) of the handling feature (201), or from the guide walls (202 or 203) as shown in the illustrated embodiment. Extending downward from the distal end of the arm is a flange (208) which incorporates a cutting blade slot (209). The blade slot (209) is adapted to guide a blade from standard oscillating surgical saw or other similar bone-cutting device (not shown) to make a set of precise parallel bone cuts in the target bone. The flange (208) may optionally comprise a secondary blade slot (210) parallel to, and located proximal of, blade slot (209) to permit for the making of additional cuts at a known offset (in this case 4 mm) from the first cut without requiring sliding of the cutting guide (200) on the bone plate (100). Similarly, additional blade slots (not shown) may optionally be included on flange (208) to make cuts at different standard offsets from the first cut.

Cutting guide (200) may also optionally include one or more Kirschner Wire (K-Wire) holes (211) on one or both of the guide walls (202,203). These K-Wire holes (211) are obliquely oriented and adapted to guide K-Wires into the target bone to temporarily lock the position of the cutting guide (200) relative to the target bone. Alternatively, the position of the cutting guide (200) may be locked by using a lock screw or clamp (not shown) between the cutting guide (200) and the bone plate (100).

Referring next to FIG. 3, shown are the sequence of steps for assembly of bone plate (100) and cutting guide (200). In the first step, the cutting guide (200) is placed directly above bone plate (100) with the guide blades (204,205) oriented downward and the opposite side (104) of bone plate (100) facing upward. Guide blades (204,205) should be aligned with track overhead entries (116). In step 2, the cutting guide is moved downward until the tracks (204,205) are resting on lower bounding walls (115). Finally, in step 3, the cutting guide (200) is slid distally in relation to bone plate (100) until the distal movement is constrained by the track limit points (119). Although this exemplary illustration demonstrates the cutting guide (200) engaging the bone plate (100) from the overhead position, the system of the present invention also permits the cutting guide (200) to engage the bone plate (100) from the rear position.

Method of Use

In operation, the following is a listing of the steps typically taken to utilize the disclosed system to perform an osteotomy on the ulnar bone and stabilize the rejoined bone:

1. To expose the ulnar bone, make a 10 cm to 12 cm longitudinal incision along the subcutaneous border of the distal to mid ulna.

2. To affix the bone plate to the ulna, use a drill of appropriate size (and optionally drill guides if using locking screws) to place two cortical screws, of appropriate lengths, into two of the distal bone screw holes (107a,107b, 107c).

3. To affix the proximal elongated slot (105): use a drill of appropriate size (and optionally drill guides if using locking screws) to place a cortical screw, of appropriate length, into the proximal long slot (105) in the most proximal position.

4. To affix the proximal elongated slot (106): use a drill of appropriate size (and optionally drill guides if using locking screws) to place a cortical screw, of appropriate length, into the proximal long slot (106) in the most proximal position.

5. Check the placement of the bone plate (100) using fluoroscopy. If misaligned, loosen screws, then readjust plate position and retighten screws.

6. To attach cutting guide (200) align and install on bone plate (100), using the procedure previously described, the appropriate cutting guide (200) (transverse (not shown) and oblique (FIGS. 1A-E, 2A-C) options are available) to the bone plate (100). Position cutting guide (200) such that proximal edge (213) is just distal of the zero-mark line (121). Use two K-Wires to temporarily fix the cutting guide (200) by driving them into the K-Wire holes (211) on the cutting guide (200) and into the bone.

7. To make the distal bone cut, using an oscillating saw (not shown), cut the ulna through blade slot (209) on the cutting guide (200). Once the ulna has been cut all the way through, remove the K-Wires.

8. Slide the cutting guide (200) proximally until the determined osteotomy length is achieved. Each laser etched indicia line (120) on the bone plate (100) corresponds to an additional osteotomy length of 2 mm. Use two K-Wires to again temporarily fix the cutting guide (200) by driving them into the K-Wire holes (211) on the cutting guide (200) and into the bone.

9. To make the proximal bone cut, using an oscillating saw (not shown), cut the ulna through blade slot (209) on the cutting guide (200). Once the ulna has been cut all the way through, remove the K-Wires. Remove the cutting guide (200) from the bone plate (100) and remove the cut bone wafer from the ulna.

10. To reduce the osteotomy, loosen the two screws in the proximal and distal elongated slots (105,106) and place one blade of an appropriately sized forceps into recess (109) and the other blade into the head of one of the loosened screws. In an alternative embodiment, the other blade of the forceps can be placed adjacent to the opposite side of the head of one of the loosened screws. In order to aid in this step, a specialized forceps may be used which has the tip of one blade shaped to mate with recess (109) and the tip of the other blade shaped to mate with either the driver pattern on the head of the screws or with the side of the head of the screws. Using the forceps, reduce and compress the ulnar fragments together until adequate compression is achieved across the osteotomy site. Tighten the two screws loosened previously in this step.

11. Use a drill of appropriate size (and optionally drill guides if using locking screws) to place one cortical screw, of appropriate length, into the remaining distal bone screw hole (107a,107b, or 107c).

12. If an oblique osteotomy cut was chosen, an oblique lag screw may be placed across the osteotomy interface. Use a drill of appropriate size to place a cortical lag screw, of appropriate length, into the oblique bone screw hole (107d) of the bone plate (100).

Check the plate and screw trajectories under fluoroscopy for adequate placement and osteotomy compression and close the incision.

Figure 5:
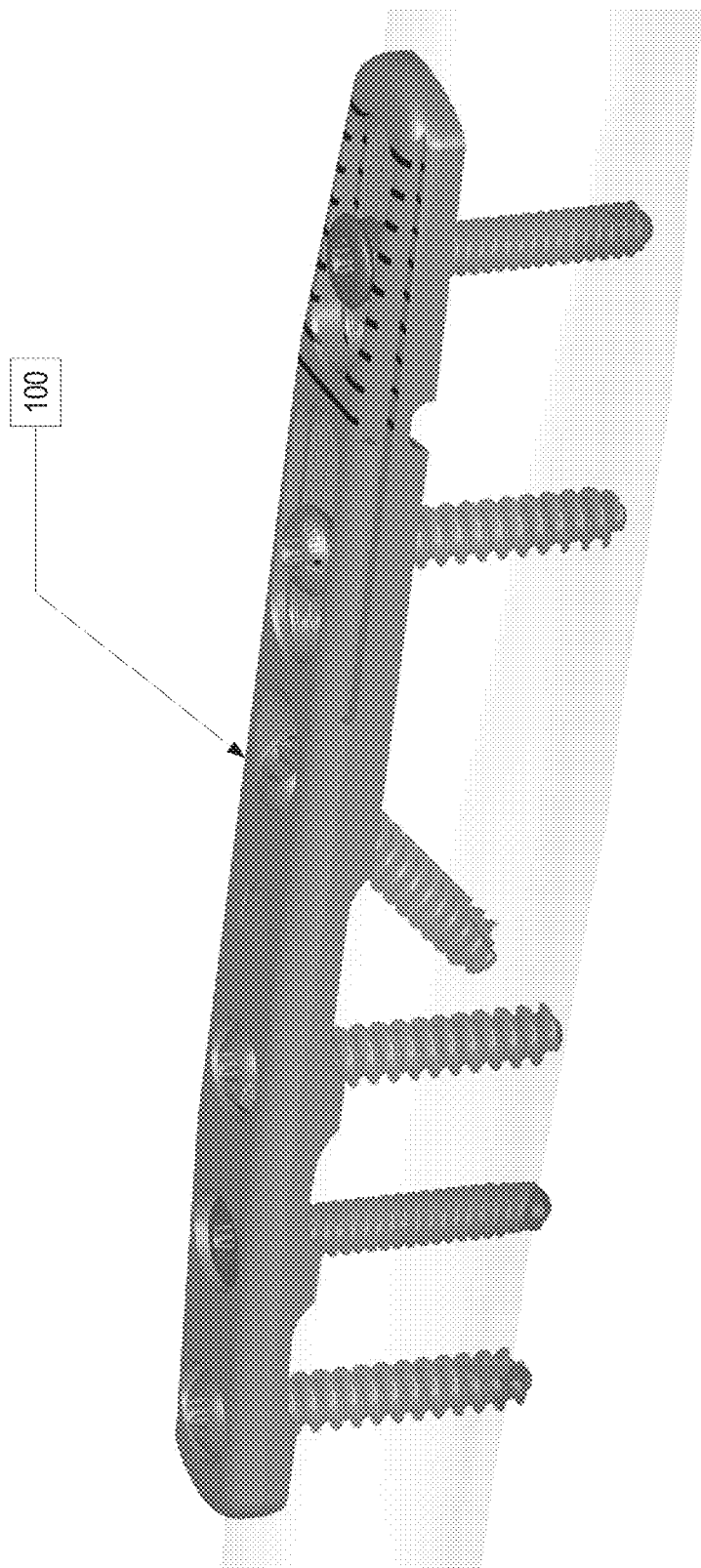
FIG. 5 illustrates the bone plate FIGS. 1A-E implanted on an ulnar bone after cutting.

Illustrated in FIG. 5 is bone plate (100) implanted on the ulnar bone after the osteotomy.

Although described above in connection with certain bone types and parts, namely the ulnar bone, these descriptions are not intended to be limiting as various modifications may be made therein without departing from the spirit of the invention and within the scope and range of equivalent of the described embodiments. Encompassed embodiments of the present invention can be used in all applications requiring osteotomy and stabilization of bones.

We claim:

1. A bone cutting system comprising:
    a substantially rigid bone plate comprising
        an elongated body having a proximal end and a distal end and defining a longitudinal body axis;
        the bone plate comprising a bone contacting side, and opposing side, a left sidewall and a right sidewall, all of which extend between the proximal end of the bone plate and the distal end of the bone plate and all of which are substantially aligned with the longitudinal body axis;
        a proximal elongated slot extending through the bone plate between the opposing side and the bone contacting side located adjacent to the proximal end of the bone plate, the proximal elongated slot adapted to receive a bone screw;
        a distal elongated slot extending through the bone plate between the opposing side and the bone contacting side and adjacent to the proximal elongated slot but located distally on the bone plate relative to the proximal elongated slot, the distal elongated slot adapted to receive a bone screw;
        one or more bone screw holes extending through the bone plate between the opposing side and the bone contacting side and located distally on the bone plate relative to the distal elongated slot, the one or more screw holes adapted to receive a bone screw;
        a recess on the opposing side of the bone plate;
        a left track recessed into the left sidewall, the left track extending longitudinally between a track limit point and the proximal end of the bone plate, the left track being bound by an upper bounding wall, and a lower bounding wall, the lower bounding wall extending for the entire length of the left track while the upper bounding wall extends partially from a distal end of the left track to a location distal to the proximal end of the left track; and
        a right track recessed into the right sidewall, the right track extending longitudinally between a track limit point and the proximal end of the bone plate, the right track being bound by an upper bounding wall, and a lower bounding wall, the lower bounding wall extending for the entire length of the right track while the upper bounding wall extends partially from a distal end of the right track to a location distal to the proximal end of the right track;
        wherein portions of the left track and the right track that are bound only by a lower bounding wall provide an overhead entry to the left track and right track accessible from the opposing side of the bone plate;
    a bone cutting guide adapted to cooperate slidingly with the bone plate, the bone cutting guide comprising
        a handling feature;
        left and right guide walls extending downwardly from the handling feature and terminating respectively in left and right horizontal guide blades, the left and right horizontal blades adapted to mate with the left and right tracks of the bone plate respectively;
        an arm extending downward from one of the handling feature, the right guide wall, and the left guide wall, and comprising a flange;
        a cutting slot disposed on the flange;

wherein when the left and right horizontal blades are engaged with the left and right tracks of the bone plate respectively; the cutting guide slides in a proximal-distal direction relative to the bone plate.

2. The bone cutting system of claim 1 wherein at least one of the proximal elongated slot and the distal elongated slot is threaded.

3. The bone cutting system of claim 1 wherein at least one of the proximal elongated slot and the distal elongated slot is unthreaded.

4. The bone cutting system of claim 1 wherein at least one of the proximal end of the bone plate and the distal end of the bone plate is tapered.

5. The bone cutting system of claim 1 wherein at least a portion of the bone contacting surface is cylindrically concave.

6. The bone cutting system of claim 1 wherein at least one of the one or more bone screw holes is threaded.

7. The bone cutting system of claim 1 wherein at least one of the one or more bone screw holes is unthreaded.

8. The bone cutting system of claim 1 wherein at least one of the one or more bone screw holes defines a screw axis that is substantially normal to the bone contacting surface.

9. The bone cutting system of claim 1 wherein at least one of the one or more bone screw holes defines a screw axis that is oblique to the bone contacting surface.

10. The bone cutting system of claim 1 wherein the recess is adapted to receive a blade tip of a forceps.

11. The bone cutting system of claim 1 wherein the bone cutting guide further comprises one or more k-wire holes through one or both of the left and right guide walls.

12. The bone cutting system of claim 1 wherein one or both of the bone plate and the cutting guide includes indicia adapted to measure the length of movement of the cutting guide with respect to the bone plate.

* * * * *